United States Patent [19]

Froehner et al.

[11] Patent Number: 4,954,436
[45] Date of Patent: Sep. 4, 1990

[54] DIHYDROPYRIDINE-SENSITIVE CALCIUM CHANNEL AS A TUMOR ASSOCIATED MARKER

[75] Inventors: Stanley C. Froehner, Hanover; Mary E. Morton, Etna, both of N.H.

[73] Assignee: Trustees of Dartmouth College, Hanover, N.H.

[21] Appl. No.: 83,239

[22] Filed: Aug. 6, 1987

[51] Int. Cl.$^5$ ................ G01N 33/53; G01N 33/566; A61K 39/00; C07K 15/14
[52] U.S. Cl. ........................................ 435/7; 424/1.1; 424/9; 435/28; 435/172.2; 435/240.77; 436/501; 436/503; 436/512; 436/548; 436/813; 530/350; 530/387; 935/106; 935/107; 935/110
[58] Field of Search ................ 424/1.1, 9, 85; 435/240, 27, 172.2, 7, 28; 438/503, 546, 548, 813; 530/387, 350; 436/501, 512; 935/106, 107, 110

[56] References Cited

U.S. PATENT DOCUMENTS

| | | | |
|---|---|---|---|
| 4,690,935 | 9/1987 | Taylor et al. | 514/356 |
| 4,784,955 | 11/1988 | Campbell | 436/538 |
| 4,784,958 | 11/1988 | Glossman | 436/504 |

OTHER PUBLICATIONS

Flockeral et al., Nature, vol. 323, Sep. 1986, pp. 66–68.
Curtis et al., Biochemistry, vol. 23, No. 10, May 1984, pp. 2113–2118.
Leung A. T. et al., J. Biol. Chem. 262(17), 1987.
Chin, H. et al., Soc. Neurosci. Abst. 13:99, 1987.
Smilowitz, J. et al.; Soc. Neurosci. Abst. 13:99, 1987.
Norman et al., FEBS Letters, vol. 212, No. 1, Feb. 1987, pp. 127–132.
Cooper et al., The Journal of Biological Chemistry, vol. 262, No. 2, Jan. 1987, pp. 509–512.
Takahashi et al., Science, vol. 236, No. 4797, Apr. 1987; pp. 88–91.

Primary Examiner—Robert J. Warden
Assistant Examiner—Florina B. Hoffer
Attorney, Agent, or Firm—Hamilton, Brook, Smith & Reynolds

[57] ABSTRACT

A protein antigen related to the dihydro-pyridine-sensitive calcium channel is expressed at high levels by small cell carcinoma of the lung and neuroblastomas. The antigen serves as a marker which can be exploited for diagnosis and therapy of these tumors. Methods of diagnosis and therapy of small cell carcinoma of the lung and neuroblastomas employing monoclonal antibodies which are specific for the dihydropyridine-sensitive calcium channel are also described.

14 Claims, 5 Drawing Sheets

FIG. 1

●——● = mab 1A

○——○ = control mab 88B

□——□ = buffer

DIHYDROPYRIDINE-SENSITIVE CALCIUM CHANNEL AS A TUMOR ASSOCIATED MARKER

GOVERNMENT SUPPORT

Work described herein was supported in part by National Institutes of Health Grant 5-RO1NS-14871.

BACKGROUND OF THE INVENTION

Voltage-sensitive calcium channels mediate the entry of calcium into many types of cells, including cardiac, skeletal, and smooth muscle as well as excitable and secretory cells. Tsien, R. W. *Annu. Rev. Physiol.* 45:341–398, 1983; Reuter, H. *Nature* 301:569–574, 1983. Dihydropyridines, such as nitrendipine, nifedipine, and PN200-110, bind with high affinity and specificity to putative calcium channels and have been used extensively as tools for the purification and characterization of these components. See e.g.,Glossmann, H., Ferry, D. R., Lubbecke, F., Mewes, R. and Hofmann, F. *Trends Pharmacol. Sci.* 3:431–437, 1982; Reuter, H., Porzig, H., Kokubun, S. and Prod'hom, B. *Trends Neurosci.* 8:396–400, 1985; and Godfraind, T., Miller, R. and Wibo, M. *Pharm. Reviews* 38:321–416, 1986.

Transverse tubules of skeletal muscle contain high concentrations of dihydropyridine-sensitive calcium channels, yet their function at these sites remains unclear (Almers, W., Fink, R. and Palade, P. T. *J. Physiol.* 312:177–207, 1981; Chiarandini, D. J. and Stefani, E. *J. Physiol.* 335:29–40, 1983; Schwartz, L. M., McClesky, E. W. and Almers, W. *Nature* 314:747–751, 1985). Highly purified preparations of dihydropyridine binding complex isolated from skeletal muscle exhibit voltage sensitive (Flockerzi, V., Oeken, H-J., Hofmann, F., Pelzer, D., Cavalie, A. and Trautwein, W. *Nature* 323:66–68, 1986) or agonist-stimulated (Curtis, B. M. and Catterall, W. A. *Biochemistry* 25:3077–3083, 1986) calcium channel activity after reconstitution. There is general agreement that a polypeptide of $M_r$ 170,000, which upon reduction is converted to a protein of $M_r$ 140,000, is a major component of this complex (Curtis, B. M. and Catterall, W. A. *Biochemistry* 23:2113–2118, 1984; Flockerzi, V., Oeken, H-J. and Hofmann, F. *Eur. J. Biochem.* 161:217–224, 1986; Striessnig, J.,-Moosburger, K., Goll, A., Ferry, D. and Glossman, H. *Eur. J. Biochem.* 161: 603–609, 1986; Borsotto, M., Barhanin, J., Fosset, M. and Lazdunski, M. *J. Biol. Chem.* 260:14255–14263, 1984). Other proteins of $M_r$ 50,000 and $M_r$ 33,000 have also been shown to be present in some preparations (Flockerzi, V., Oeken, H-J., Hofmann, F., Pelzer, D., Cavalie, A. and Trautwein, W. *Nature* 323:66–68, 1986; Curtis, B. M. and Catterall, W. A. *Biochemistry* 23:2113–2118, 1984). However, there is considerable dispute as to the association of these components with the channel (Vandaele, S., Fosset, M., Galizzi, J-P. and Lazdunski, M. *Biochemistry* 26:5–9, 1987).

The development of the monoclonal technique has greatly facilitated the search for phenotype heterogeneity of tumors and normal tissues and the recognition of tumor associated antigens. However, the number of tumor associated antigens identified is still limited. Identification of additional tumor-associated antigens will improve differential diagnosis and classification of tumors which in turn will provide better modes of treatment of tumors.

SUMMARY OF THE INVENTION

This invention pertains to monoclonal antibodies which are specific for the dihydropyridine-sensitive calcium channel. This invention also pertains to methods of detection, diagnosis and treatment of small cell carcinoma of the lung, neuroblastoma, and other tumors which express a surface protein recognized by the antibodies against dihydropyridine-sensitive calcium channel. The invention is based on the discovery that a surface protein recognized by antibody against dihydropyridine-sensitive calcium channel is expressed at high levels by certain tumor cells. This association provides a basis for differentiating between cancer cells that express high levels of the surface protein and normal cells or other tumor cells (which either do not express the surface protein or do not express it at significant levels). For example, a high level of expression of the channel is associated with small cell carcinoma of the lung and neuroblastoma. Thus, the protein can be exploited as a marker for these tumors in diagnosis and therapy.

Monoclonal antibodies specific for the dihydropyridine-sensitive calcium channel are particularly useful in the method of this invention. For example, these antibodies can be used to image primary and/or metastatic small cell carcinoma of the lung or neuroblastoma in vivo by immuno-scintigraphy and thereby allow tumor localization. In addition, antibody specific for the dihydropyridine-sensitive calcium channel antigen can be used to detect the presence of small cell carcinoma or neuroblastoma in tissue specimens. In therapy, the antibody may be used for passive immunotherapy, or as a targeting agent for selective delivery of cytotoxic agents to a tumor in vivo. In addition, the antibody provides a means of targeting effector cells (e.g. macrophages) against tumor cells which express the dihydropyridine-sensitive calcium channel antigen.

DETAILED DESCRIPTION OF THE INVENTION

It has now been discovered that a surface protein recognized by antibodies against the di- hydropyridine-sensitive calcium channel is associated with certain forms of tumor, particularly small cell carcinoma of the lung and neuroblastoma. This association can be exploited for diagnosis and therapy of these tumors (and other tumors which exhibit distinguishable levels of the calcium channel). Many of the diagnostic and therapeutic methods described herein contemplate the use of antibody, particularly monoclonal antibody, which binds specifically to the dihydropyridine-sensitive calcium channel or a component subunit thereof. However, other reagents which can be used to exploit the protein with which these antibodies are reactive as a tumor marker are intended to be encompassed by this invention.

Dihydropyridine-sensitive binding complex, purified from rabbit muscle transverse tubule membranes was used as immunogen for the production of monoclonal antibodies. Hybridoma culture supernatants were screened initially by a dot blot assay against the immunogen. Positive hybridomas were then assayed for secretion of antibodies that immunoprecipitated detergent solubilized dihydropyridine ([$^3$H]PN200-110) complexes. Three hybridoma lines exhibiting this activity were obtained. After subcloning, each line secreted a monoclonal antibody, designated mab 1A (ATCC designation HB 10047), mab 2B, and mab 20A, respectively.

[$^3$H]PN200-110 complex purified by WGA (wheat germ agglutinin) chromatography sedimented primarily as a single peak of approximately 21S in sucrose gradients containing digitonin. Gel electrophoresis after reduction with dithiothreitol (DTT) and denaturation in SDS showed that several polypeptides co-sedimented with purified [$^3$H]PN200-110 complex. Proteins of $M_r$ 200,000, 143,000, 61,000, and 33,000 were present only in the fractions corresponding to the 21S complex. Western blot analysis showed that mab 1A and mab 2B recognized the broad double band of $M_r$ 200,000, and mab 20A recognized the polypeptide that shifts from $M_r$ 220,000 to 143,000 upon reduction.

There is a direct correlation between the percent of fluorescent cells detected in a fluorescence-activated cell sorter (FACS) analysis of a small cell carcinoma cell line incubated with a monoclonal antibody to the dihydropyridine-sensitive calcium channel (e.g. mab 1A) and a FACS analysis of a small cell line incubated with a monoclonal antibody to small cell carcinoma of the lung (e.g., SCCL 1). In addition, the antibody can differentiate small cell carcinoma of the lung from squamous cell carcinoma of the lung and from an undefined lung cancer. The anti-channel antibody is also reactive with neuroblastoma.

Monoclonal antibodies which specifically bind to the channel (e.g., mab 1A, mab 2B, and mab 20A) can be used for the diagnosis and/or treatment of small cell carcinoma of the lung, neuroblastoma and other tumor cells which express the calcium channel at high levels. In the diagnostic area, antibody against the dihydropyridine-sensitive calcium channel can be used for in vivo tumor imaging to localize primary or metastatic small cell carcinoma of the lung or to monitor metastasis of the tumor. An antibody specific for the calcium channel (e.g., mab 1A, mab 2A, and mab 20A), or preferably an antigen binding fragment thereof, is conjugated to a label which generates a signal detectable by external scintigraphy (e.g. a gamma emitting radioisotope) and administered to an individual to be diagnosed. After sufficient time to allow the labeled antibody to localize at the tumor site (or sites), the signal generated by the label is detected by a photoscanning device. The detected signal is then converted to an image of the tumor. This image makes it possible to localize the tumor in vivo which can aid in determining an appropriate therapeutic strategy.

Antibody fragments, rather than whole antibody molecules, are generally preferred for use in tumor imaging. Because they are distributed more readily in the tissues than are entire antibody molecules, antibody fragments accumulate at the tumor(s) more rapidly. Thus an image can be obtained in less time than is possible using whole antibody. These fragments are also cleared more rapidly from tissues, resulting in a lower background signal. Haber et al., U.S. Pat. No. 4,036,945; Goldenberg et al., U.S. Pat. No. 4,331,647. The divalent antigen binding fragment (Fab')$_2$ and the monovalent Fab are especially preferred. Such fragments can be prepared by digestion of the whole immunoglobulin molecule with the enzyme pepsin or papain according to any of several well known protocols.

The antibodies or antibody fragments can be labelled with radioisotopes such as Iodine-131, Indium-111 and Technetium-99m. The gamma-emitters Indium-111 and Technetium-99m are preferred because these radiometals are detectable with a gamma camera and have favorable half lives for imaging in vivo. Antibody can be labelled with Indium-111 or Technetium-99m via a conjugated metal chelator, such as DTPA (diethylenetriaminepentaacetic acid). Krejcarek et al., *Biochem. Biophys. Res. Comm.* 77:581, 1977; Khaw, B. A. et al. *Science* 209:295, 1980; Gansow et al., U.S. Pat. No. 4,472,509; Hnatowich, U.S. Pat. No. 4,479,930, the teachings of which are incorporated by reference herein.

Human tissue specimens (e.g., biopsy samples) can be tested for high expression levels of the dihydropyridine-sensitive calcium channel by using monoclonal antibodies (e.g., mab 1A, mab 2A, and mab 20A) in an immunohistochemical technique, such as the immunoperoxidase staining procedure. Alternatively, immunofluorescent techniques can be used to examine human tissue specimens. In a typical protocol, slides containing cryostat sections of frozen, unfixed tissue biopsy samples or cytological smears are air dried, and then incubated with the anti-dihydropyridine-sensitive calcium channel antibody preparation in a humidified chamber at room temperature. The slides are layered with a preparation of fluorescently labelled antibody directed against the monoclonal antibody. The staining pattern and intensities within the sample are determined by fluorescent light microscopy.

The antibodies which specifically bind to the dihydropyridine-sensitive calcium channel can be used in different forms of therapy for treatment of small cell carcinoma of the lung and neuroblastoma. For one, antibody can be used to passively immunize against a tumor. In passive immunotherapy, an anti-tumor amount of the monoclonal antibody is administered in a physiologically acceptable vehicle (e.g., normal saline) to a patient afflicted with small cell carcinoma of the lung. Intact antibody is generally used for this purpose because effector functions attributable to the $F_c$ portion are retained.

Monoclonal antibodies which specifically bind to the dihydropyridine-sensitive calcium channel can be used as targeting agents to deliver anti-cancer agents selectively to tumor cells. Various pharmaceutical or cytotoxic agents can be covalently or noncovalently coupled to the antibodies to form an antibody conjugate. Examples of useful therapeutic agents include: radioactive compounds (e.g., $^{125}I$, $^{131}I$); agents which bind DNA, such as alkylating agents or various antibodies (e.g., daunomycin, adiamycin, chlorambucil); antimetabolites (e.g., methotrexate); and inhibitors of protein synthesis (e.g., diptheria toxin and toxic plant proteins). Methods of forming these conjugates are known in the art. See e.g. Rodwell et al., U.S. Pat. No. 4,671,958.

Antibodies which specifically bind to the channel also can be used to target human effector cells (e.g., macrophages, cytotoxic T cells) against tumor cells. For this purpose bifunctional anti-bodies can be produced which have an anti-calcium channel specificity and an anti-effector cell specificity. For example, an anti-channel antibody (or an antigen binding region derived from an anti-channel antibody) can be coupled to an antibody against $F_c$ receptor of a human effector cell. The conjugate so formed can be used to arm an effector cell. The effector cells either lyse or phagocytose the target cells, depending upon the effector cell type, the target cell type and the specific $F_c$ receptor type involved. The conjugate so formed can be used to arm an effector cell which expresses $F_c$ receptor. Monoclonal antibodies which are specific for the $F_c$ receptor of human effector cells are described by Fanger, Guyre and Anderson in U.S. patent Ser. No. 069,412, filed July 1, 1987, the teachings of which are incorporated by reference herein. See also, Anderson, C. et al., *J. Biol. Chem.* (1986). Examples of antibodies described in this application are mab 32, mab 22, mab 44, mab 62 and mab 197. These are particularly useful antibodies for effector cell targeting because the binding of these antibodies to effector cells is not blocked by physiological concentrations of IgG. As a specific example, the anti-calcium channel antibody 1A can be coupled to mab 32 to produce a 1A×32 heteroantibody. The 1A×32 heteroantibody can be bound to a human macrophage to target the macrophage for small cell carcinoma of the lung or neuroblastoma.

The invention is illustrated further by the following examples.

EXAMPLE 1: Production of monoclonal antibody; Identification of a 200 kDa Subunit of the Dihydropyridine-Sensitive Calcium Channel

Transverse tubule purification

Rabbit muscle transverse tubules were prepared according to Fernandez et al. (Fernandez, J. L., Rosemblatt, M., and Hildalgo, C. *Biochem. Biophys. Acta* 599:552-568, 1980) with the addition of the following reagents to inhibit protease activity: 1.0 mM phenylmethylsulfonyl fluoride, 1.0 uM pepstatin A, 10 units/ml aprotinin, 5.0 mM iodoacetamide, 10 mM EDTA, 10 mM EGTA. After 0.5 M KCl treatment and centrifugation, pellets were washed once in buffer A (10 mM $NaPO_4$, pH 7.4, 0.15M NaCl, 0.02% $NaN_3$, plus protease inhibitors). This material was used immediately.

In some cases, transverse tubule membranes were purified further in the following manner. Membranes after 0.5M KCl treatment were resuspended to 20 ml in buffer B (0.02M Tris-maleate, pH 7.0, containing protease inhibitors) and layered on 4-20 ml sucrose cushions (27.5% [w/w] sucrose in buffer B). After centrifugation for 1 hour at 300,000×g (Beckman 60 Ti rotor), the band at the buffer B/sucrose interface was removed and washed once with buffer B by centrifugation. This material was either used immediately or stored at −70° C.

[$^3$H]PN200-110 complex solubilization and purification on WGA-Sepharose

Purification of dihydropyridine binding complexes was based on the method of Curtis, B.M. and Catterall, W. A. *Biochemistry* 23:2113-2118, 1984. Membranes were resuspended at a concentration of 5 mg protein/ml in buffer A, incubated with [$^3$H]PH200-110 (10 nM final concentration; Amersham) for 30 minutes in the dark at 4° C., washed by centrifugation, and resuspended in buffer A containing 1% digitonin (Sigma; purified according to Bridges, C. D. B. *Vision Res.* 17:301-302, 1977) at 2.3 mg protein/ml. After 30 minutes, insoluble material was removed by centrifugation at 50,000×g for 30 minutes, the supernatant was diluted with an equal volume of buffer A, and the sample was incubated for 30 minutes with 7 to 10 ml WGA-Sepharose. The column was washed with 5 volumes of buffer A containing 0.1% digitonin and then eluted with buffer A containing 100 mM N-acetyl-D-glucosamine and 0.1% digitonin. Fractions containing the complex were identified by liquid scintillation counting, and the peak fractions were pooled.

Sucrose gradient sedimentation

Sucrose velocity gradient analyses were performed to establish that mab IA recognizes the purified complex previously shown by others to possess calcium channel activity (Flockerzi, V., Oeken, H-J., Hofmann, F., Pelzer, D., Cavalie, A. and Trautwein, W. *Nature* 323:66-68, 1986; Curtis, B. M. and Catterall, W. A. *Biochemistry* 25:3077-3083, 1986).

Up to 2.0 ml of the pooled fractions from the WGA column were layered onto a 25 ml gradient of 5-20% sucrose in buffer A containing 0.1% digitonin. Gradients were centrifuged for 90 min at 300,000×g in a Beckman 60 Ti rotor. Fractions (1 ml) were collected from the bottom of the tubes and liquid scintillation counting was used to identify fractions containing the complex. For SDS gel and Western blot analysis, fractions were dialyzed twice for 60 minutes against 0.1 mM Tris pH 7.4, 0.1% SDS, 10 mM EDTA, 10 mM EGTA, 5 mM iodoacetamide (dialysis buffer), lyophilized, resuspended in SDS gel electrophoresis sample buffer, with or without 50 mM DTT, and boiled for 3 minutes.

Production and selection of monoclonal antibodies

Balb/c mice were injected with material solubilized from purified transverse tubules and isolated by WGA-Sepharose chromatography and sucrose gradient centrifugation. All procedures were carried out as previously described for the acetylcholine receptor. See Froehner, S. C., Douville, K., Klink, S. and Culp, W. J. *J. Biol. Chem.* 258: 7112,7120, 1983.

Dot blot analysis was used as the initial screen. Peak fractions from the sucrose gradient were pooled, 20 ul were spotted onto nitrocellulose in wells of a microtiter plate (Millipore Millititer HA), and air dried. Wells were blocked, incubated with hybridoma culture supernatants (50 ul) for 2 hours at 37° C., and washed as previously described (Froehner, Douville et al.) Alkaline phosphatase-conjugated goat-anti-mouse IgG (Hyclone; 100 ul of 1/100 dilution) was then added to the wells, incubated for 2 hours, washed, and developed (Blake, M. S., Johnson, K. H., Russell-Jones, G. J. and Gotschlich, E. C. *Anal. Biochem.* 136:175-179, 1984).

Culture supernatants that were positive in the dot blot assay were assayed for their ability to immunoprecipitate detergent-solubilized [$^3$H]PN200-110 complexes. Complexes were prepared as described above by labeling purified transverse tubule membranes with [$^3$H]PN200-110 and solubilizing with 1% digitonin. In a 1.5 ml eppendorf tube, 10 ul of complex were incubated with 100 ul hybridoma supernatant for 1 hour at 4° C. in the dark. IgGSorb (40 ul) coupled to rabbit anti-mouse IgG (Froehner, S. C., Murnane, A. A., Tobler, M., Peng, H. B. and Sealock, R. *J. Cell. Biol.* 104:163, 1987) was added and the incubation continued for 30 minutes. The volume was brought to 1.0 ml with buffer A and underlaid with 100 ul 60% (w/w) sucrose, 0.1% digitonin in buffer A. Samples were centrifuged for 10 minutes in a microfuge, the supernatant was removed by aspiration, and the pellets were resuspended and counted by liquid scintillation.

Immunoaffinity chromatography

Immunoaffinity chromatography was performed at 4° C. as described by LaRochelle, W. J. and Froehner S. C. (*J. Biol. Chem.*, 262:8190–8195, 1987), with modifications, as a further test of the association of the other proteins with the $M_r$ 200,000 polypeptide bearing the 1A epitope. Antibody affinity columns were prepared by coupling mab 1A IgG or mab 1403 IgG to BioRad Affigel 10. See LaRochelle and Froehner. ibid, et al. Mab 1403, an IgG-1 isotype, recognizes an intermediate filament protein in skeletal muscle. It was used in these experiments as a control antibody. Material solubilized from crude transverse tubules was purified first by WGA chromatography and then was incubated for 1 hour with either mab 1A-Affigel (2 ml) or control mabAffigel (2 ml). The columns were washed sequentially with 25 ml buffer A containing 0.1% digitonin, 25 ml buffer A containing 0.1% digitonin and 1.0 M NaCl, and 25 ml buffer A (no digitonin). The columns were then eluted with 100 mM ammonium acetate, pH 11.5. The eluate was neutralized immediately and lyophilized. The sample was dissolved in 1 ml dialysis buffer (see above) and dialyzed twice for 90 minutes against dialysis buffer, and lyophilized prior to SDS gel electrophoresis.

SDS gel electrophoresis and Western blotting

Gel electrophoresis in SDS and Western blot analysis were performed as previously described (Froehner, S. C., Douville, K., Klink, S. and Culp, W. J. *J. Biol. Chem.* 258:7112–7120, 1983) The following proteins were used as molecular weight markers: alpha and beta spectrin from human erythrocytes ($M_r$ 240,000, $M_r$ 220,000), myosin ($M_r$ 205,000), *E. coli* beta-galactosidase ($M_r$ 116,000), and subunits of Torpedo acetylcholine receptor ($M_r$ 64,500, $M_r$ 60,500, $M_r$ 53,000, $M_r$ 45,900. See Froehner, S. C., and Rafto, S. *Biochemistry* 18:301–307, 1979. Gels were silver stained according to BioRad Bulletin 1089.

Results

The purified [$^3$H]PN200-110 binding component was used as immunogen for the production of monoclonal antibodies. Hybridoma culture supernatants were screen first by a dot blot assay against the material used as immunogen. Positive hybridomas were then assayed for secretion of antibodies that immunoprecipitated detergent-solubilized [$^3$H]PN200-110 complexes. Three hybridoma lines exhibiting this activity were obtained. After subcloning, these lines secreted IgG-1 antibodies, designated mab 1A, mab 2B and and IgG2a designated mab 20A.

Figure 1:
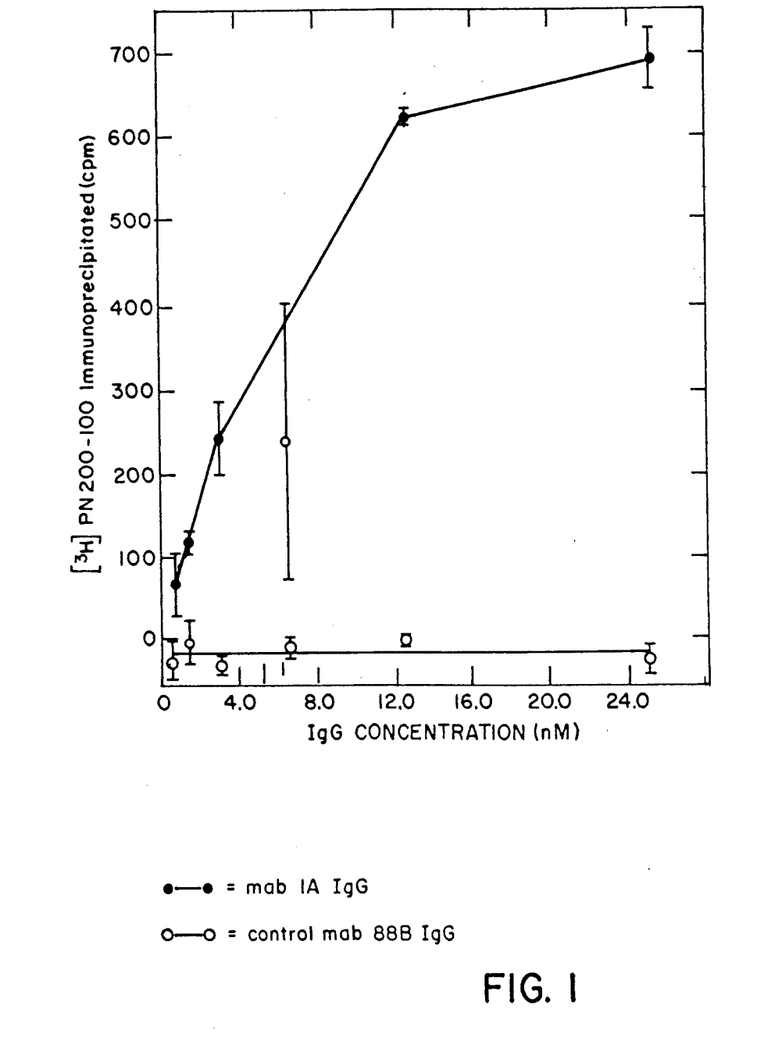
FIG. 1 depicts the immunoprecipitation of [$^3$H]PN200-110 complex with mab 1A.

FIG. 1 shows that: (a) mab 1A immunoprecipitated [$^3$H]PN200-110 complexes in a specific and saturable manner, and (b) no precipitation occurred with mab 88B, a control mab IgG of the same isotype which recognizes the nicotinic acetylcholine receptor (Froehner, S. C., Douville, K., Klink, S. and Culp, W. J. *J. Biol. Chem.* 258:7112-7120, 1983). From the concentration needed to obtain half-maximal precipitation, mab 1A appears to have an affinity of approximately 5 nM for [$^3$H]PN200-110 complexes. In no case did mab 1A immunoprecipitate all of the [$^3$H]-dihydropyridine This is most likely due to dissociation of the drug from the complex. However, it is also possible that mab IA recognizes a subset of [$^3$H]PN200-110 complexes. To establish that mab 1A recognizes the purified complex previously shown by others to possess calcium channel activity (Flockerzi, V., Oeken, H-J., Hofmann, F., Pelzer, D., Cavalie, A. and Trautwein, W. *Nature* 323:66–68; Curtis, B. M. and Catterall, W. A. *Biochemistry* 25:3077–3083, 1986) sucrose velocity gradient analyses were performed.

Figure 2:
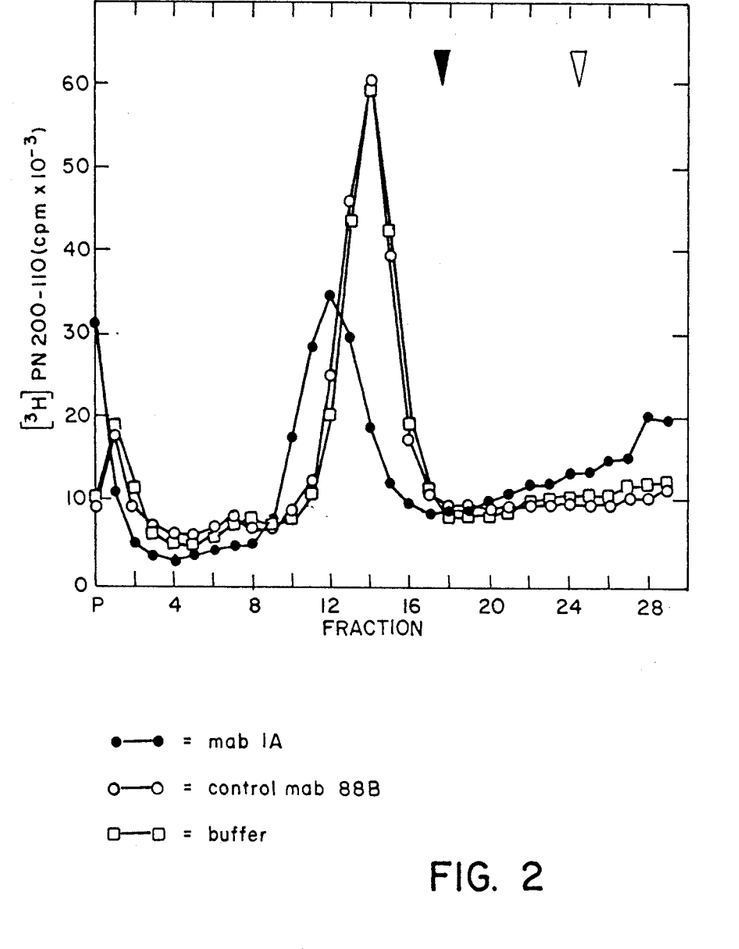
FIG. 2 depicts the effect of mab 1A on the sucrose gradient sedimentation of the [$^3$H]PN200-110 complex.

In agreement with published reports (Curtis, B. M. and Catterall, W. A. *Biochemistry* 23: 2113–2118, 1984; Flockerzi, V., Oeken, H. J. and Hofmann, F. *Eur J. Biochem* 161:217–224, 1986; Striessnig, J., Moosburger, K., Goll, A., Ferry, D. and Glossmann, H. *Eur. J. Biochem.* 161:603–609, 1986) [$^3$H]PN200-110 complex purified by WGA chromatography sedimented primarily as a single peak of approximately 21S in sucrose gradients containing digitonin. (See FIG. 2; Marker enzymes beta-galactosidase [15.9S, solid arrow] and alkaline phosphatase [6S, open arrow] were run in a parallel gradient.) This sedimentation behavior was unaffected by prior incubation of the complex with 183 nM mab 88B (control mab IgG). However, after incubation with 183 nM mab 1A, most, if not all, of the [$^3$H]PN200-110 complexes sedimented as a larger component of approximately 24S. The amount of radioactive material that sedimented to the bottom of the centrifuge is also increased. The positions of marker enzymes were identical in each of the three gradients. These results were highly reproducible and were observed in six separate experiments with IgG concentrations of 20–180 nM. Thus, mab IA recognized the major [$^3$H]PN200-110 binding complex purified from rabbit skeletal muscle.

Figure 3A:
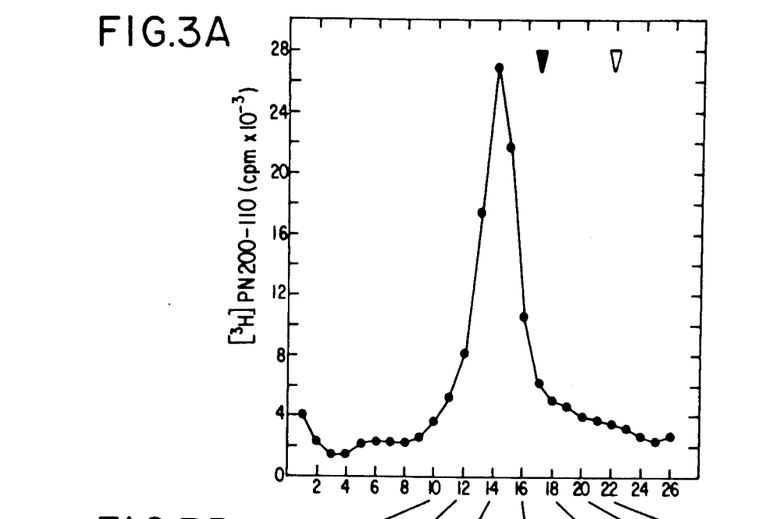
FIG. 3A depicts the sedimentation on a sucrose gradient of [$^3$H]PN200-100 complex purified by WGA chromatography.
Figure 3B:
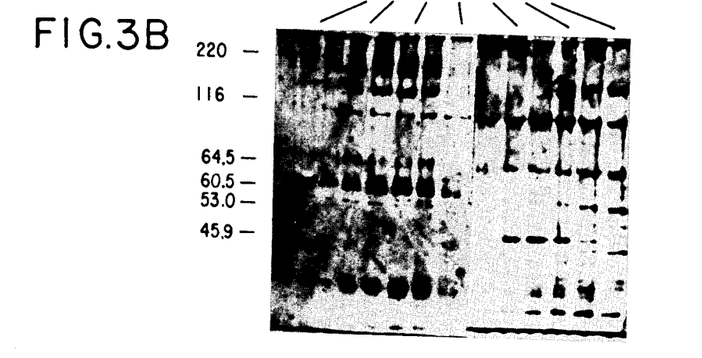
FIG. 3B is a photograph of a silver-stained SDS gel of selected fractions from the sucrose gradient shown in 3A.
Figure 3C:
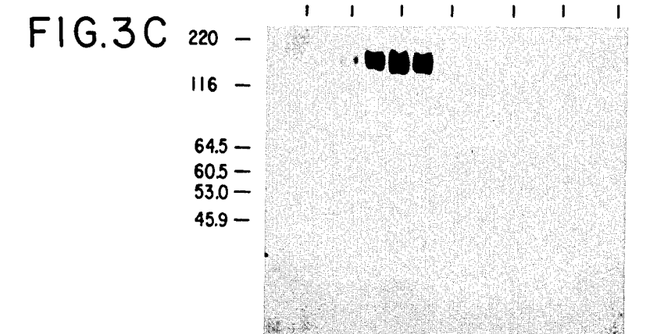
FIG. 3C is a Western blot analysis of the gel shown in 3B, using 20 nM of mab 1A IgG.
Figure 3D:
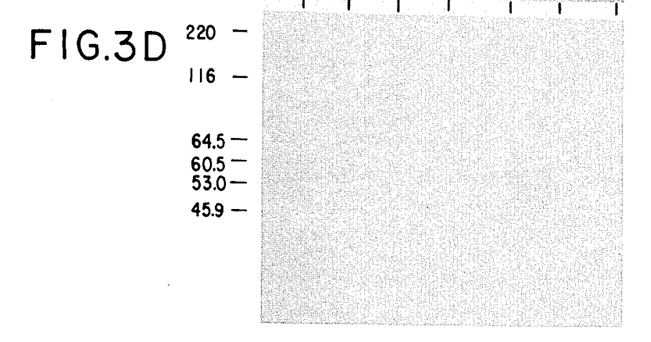
FIG. 3D is a Western blot analysis of the gel shown in 3B, using 20 nM of control mab 1403 IgG.

The sucrose gradient sedimentation of [$^3$H]PN200-110 is illustrated again in FIG. 3A. Gel electrophoresis after reduction with DTT and denaturation in SDS showed that several polypeptides co-sedimented with purified [$^3$H]PN200-110 complex. As shown in FIG. 3B, proteins of $M_r$ 200,000, 143,000, 61,000 and 33,000 were present only in the fractions corresponding to the 21S complex (fractions 12–16). In most cases, the $M_r$ 200,000 protein migrated as a broad double band. Other proteins, particularly one of $M_r$ 110,000, sedimented much more slowly and were well-resolved from the [$^3$H]PN200-110 complex. Western blot analysis showed that mab 1A (20 nM) recognized the broad double band of $M_r$ 200,000 (FIG. 3C); control mab 1403 (20 nM) did not recognize any of the bands (FIG. 3D).

As a further test of the association of the other proteins with the $M_r$ 200,000 polypeptide bearing the 1A epitope, we performed immunoaffinity chromatography. Material solubilized from crude transverse tubules with digitonin was purified by WGA chromatography, divided into two equal parts, and applied either to a mab 1A-Affigel column or to a control mab 1403-Affigel column. After extensive washing, the columns were eluted with alkaline pH buffer, and the eluates were examined by gel electrophoresis. FIG. 4A is a silver stained SDS gel of the material purified on the mab 1A-Affigel (lanes 1 and 2) and the control mab 1403-Affigel (lanes 3 and 4). Prior to electrophoresis samples were denatured by boiling in SDS sample buffer without reducing agent (lanes 1 and 3) or containing 50mM DTT (lanes 2 and 4). The polypeptide composition of material eluted from the mab 1A column is very similar to that purified by a combination of WGA chromatography and sucrose gradient centrifugation. Western blot analyses showed that mab 1A recognized the $M_r$ 200,000 polypeptide(s) and that the apparent molecular weight of this protein(s) was unaffected by reduction. In contrast, the electrophoretic migration of the $M_r$ 143,000 polypeptide was dependent on prior reduction with DTT. Without reduction, it migrated as a protein of $M_r$ 220,000. Neither of these proteins was present in material eluted from the control column (FIG. 4A; lanes 3 and 4).

Figure 4:
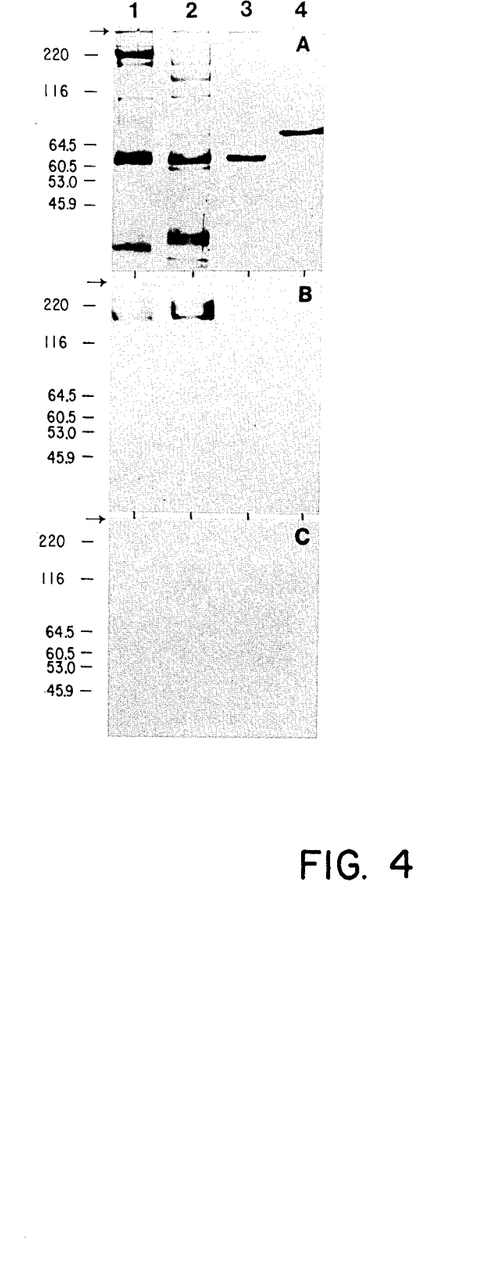
FIG. 4A is a photograph of a silver-stained SDS gel of immunoaffinity purified [$^3$H]PN200-110 complex.
FIG. 4B is a Western blot analysis of the gel shown in 4A, using 20 nM of mab 1A IgG.
FIG. 4C is a Western blot analysis of the gel shown in 4A, using 20 nM of control mab 1403 IgG.

The $M_r$ 61,000 and $M_r$ 33,000 polypeptides were also major components of the immunoaffinity-purified material. A protein of approximately $M_r$ 63,000 (under non-reducing conditions) was also eluted from the control column (FIG. 4A; lane 3). Upon reduction, this protein migrated as a larger protein (FIG. 4A; lane 4). The $M_r$ 61,000 protein eluted from the mab 1A column was unaffected by reduction (FIG. 4A; lanes 1 and 2). Thus, it appears that two poorly resolved proteins were present in the immunoaffinity isolated material: a major one of $M_r$ 61,000 that specifically purifies in association with the $M_r$ 200,000 polypeptide, and a minor contaminating protein. None of these proteins was recognized by the control mab 1403 (FIG. 4C). However, a minor polypeptide that migrated between the $M_r$ 220,000 polypeptide and the top of the separation gel (FIG. 4, lane 1) was recognized by both mab 1A and mab 1403 and, thus, may bind antibodies non-specifically.

The purification procedures we used were designed to minimize proteolytic degradation that may occur during isolation of membrane proteins from skeletal muscle, a rich source of proteases. The entire procedure requires only about 8 hours, and at all steps, including the isolation of membranes, calcium-free buffers containing several protease inhibitors were used. The polypeptide composition of the [$^3$H]PN200-110 complex associated with the voltage-dependent calcium channel described here is similar in some ways to reports from other laboratories. Curtis and Catterall (Curtis, B. M. and Catterall, W. A. Biochemistry 23: 2113-2118, 1984) described a preparation containing three major polypeptides of $M_r$ 130,000, $M_r$ 50,000 and $M_r$ 33,000, which co-purify through several purification steps and co-sediment on sucrose gradients. Under non-reducing conditions, the $M_r$ 130,000 subunit migrated as $M_r$ 160,000. Preparations similar to this have been shown to exhibit voltage-sensitive (Flockerzi, B., Oeken, H-J., Hofmann, F., Pelzer, D., Caralie, A. and Trautwein, W. Nature 323:66-68, 1986) and agonist-stimulated (Curtis B. M. and Catterall, W. A. Biochemistry 25:3077-3083, 1986) channel activity after reconstitution. Using a monoclonal antibody that immunoprecipitates the PN200-110 complex but whose polypeptide specificity remains unknown, Vandaele, S., Fosset, M., Galizzi, J-P., and Lazdunski, M., Biochemistry 26:5-9, 1987, also isolated a large subunit of $M_r$ 170,000 which is readily converted proteolytically to two disulfide-linked fragments of $M_r$ 140,000 and $M_r$ 30,000, depending on the detergent used for solubilization. They conclude that the $M_r$ 170,000 polypeptide is the dihydropyridine receptor and that the polypeptides of $M_r$ 50,000 and $M_r$ 33,000 are not a part of the receptor complex.

The mobility of the $M_r$ 220,000 polypeptide in our preparation is also affected by disulfide bond reduction, converting it to a polypeptide of $M_r$ 143,000. Therefore, this could be the large subunit of the calcium channel reported by others, although the molecular weight that we observe under nonreducing conditions is considerably larger that previously described (Curtis, B. M. and Catterall, W. A. Biochemistry 23:2113-2118, 1984; Flockerzi, V., Oeken, H-J, and Hofmann, F. Eur. J. Biochem. 161:217-224, 1986; Borsotto, M., Barhanin, J., Fosset, M. and Lazdunski, M. J. Biol. Chem. 260: 14255-14263, 1984). This may be a consequence of differences in the conditions used for gel electrophoresis. Whether the mobility differences produced by reduction are due to proteolytic activity, release of a small polypeptide, or other factors remains to be determined.

The mobility of the $M_r$ 200,000 polypeptide, the component recognized by mab 1A, is unaffected by reduction. It seems highly unlikely that it is derived from the $M_r$ 220,000 polypeptide since mab 1A does not recognize the larger protein. Thus, the $M_r$ 200,000 polypeptide appears to be a component of the dihydropyridine binding/calcium channel complex not previously described. Since virtually all of the [$^3$H]PN200-110 complex sediments as a larger complex when bound to mab 1A, the $M_r$ 200,000 polypeptide is not restricted to a minor subset of the drug binding activity. Furthermore, in view of their co-sedimentation on sucrose gradients and their co-purification through WGA chromatography and mab 1A immunoaffinity chromatography, the proteins of $M_r$ 220,000, $M_r$ 61,000, and $M_r$ 33,000 all appear to exist in a complex with the $M_r$ 200,000 polypeptide. Further investigation is needed to determine if the two smaller proteins are derived from either of the larger ones. Monoclonal antibodies against each of these polypeptide chains will be useful in these and other studies of the voltage-sensitive calcium channel associated with this complex.

Example 2: FACS Analysis of Cancer Cell Lines

Cancer cell lines were established at Dartmouth Medical School and several have been previously described. See, Pettengill, O. S., Sorenson, G. D. et al., Cancer, 45:906 (1980); Pettengill, O. S., Faulkner, C. S. et al. J. Natl. Cancer Inst. 58:511 (1977). Cells were collected, washed, and incubated with either a monoclonal antibody raised against a human small cell carcinoma cell line (SCCL1), 1A (anti-calcium channel), or control antibody. $10^6$ cells were labeled with a final concentration of 10 ug/ml IgG for 45 minutes on ice. After washing in cold PBS (0.1% BSA-0.05% azide), cells were incubated an additional 45 minutes on ice with 1/20 dilution of fluoresceinisothiocyanate (FITC)conjugated goat-anti-mouse (Fab')$_2$IgG. After a final wash, cells were resuspended in PBS and subjected to FACS analysis to determine their mean fluorescence intensity (MFI) as compared to control values and percent positive fluorescent cells (See Table I).

TABLE I

| Cell Line | Mab | MFI | % Positive |
| --- | --- | --- | --- |
| DMS 92 | SCCL1 | 187 | 34 |

TABLE I-continued

| Cell Line | Mab | MFI | % Positive |
|---|---|---|---|
| (small cell) | 1A | 175 | 28 |
|  | Control | 59 | 5 |
| DMS 153 | SCCL1 | 150 | 29 |
| (small cell) | 1A | 227 | 47 |
|  | Control | 115 | 19 |
| DMS 406 | SCCL1 | 130 | 21 |
| (small cell) | 1A | 138 | 20 |
|  | Control | 37 | 3 |
| DMS 114* | SCCL1 | 442 | 54 |
| (small cell) | 1A | 260 | 32 |
|  | Control | 66 | 4 |
| DMS 273* | SCCL1 | 361 | 51 |
| (small cell) | 1A | 394 | 47 |
|  | Control | 118 | 8 |
| A599 | SCCL1 | 33 | 9 |
| (undefined | 1A | 55 | 16 |
| lung cancer) | control | 32 | 10 |
| SQUCA | SCCL1 | 36 | 5 |
| (squamous cell) | 1A | 49 | 7 |
|  | control | 30 | 3 |
| IMR 32 | SCCL1 | 29 | 2 |
| (neuroblastoma) | 1A | 135 | 65 |
|  | control | 34 | 5 |

*Representative of three separate FACS analyses.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A monoclonal antibody which is specific for the 200kDa polypeptide of the dihydropyridine-sensitive calcium channel, the molecular mass of which remains unafffected by disulfide bond reduction.

2. A monoclonal antibody which binds specifically to the dihydropyridine-sensitive calcium channel consisting of mab 1A produced by hybridoma cell line, ATCC Number HB 10047.

3. Hybridoma cell line ATCC Number HB 10047.

4. A method of differentiating between small cell carcinoma of the lung and normal cells or other types of lung cancer cells in a patient, comprising obtaining cell specimens and determining the level of expression of a surface protein recognized by antibody against the 200 kDa polypeptide of the dihydropyridine-sensitive calcium channel by the cells, and comparing the level of expression of this surface protein among the cells, a high level of expression of the surface protein being indicative of small cell carcinoma of the lung.

5. A method of imaging a tumor which express high levels of a surface protein recognized by antibody against the dihydro-pyridine-sensitive calcium channel, comprising the steps of:

a. administering to an individual suspected of having the tumor a diagnostically effective amount of radiolabeled monoclonal antibody, or fragment thereof, which specifically binds to the 200 kDa polypeptide the dihydropyridine-sensitive calcium channel;

b. allowing the radiolabeled antibody or fragment to accumulate at a tumor site;

c. detecting the signal generated by the label by means of a photo-scanning device; and d. converting and detected signal to an image of the tumor.

6. A method of claim 5, wherein the tumor is small cell carcinoma of the lung or neuroblastoma.

7. A method of claim 5, wherein the monoclonal antibody is produced by hybridoma cell line ATCC No. HB b 10047.

8. A method of claim 5, wherein a (Fab')$_2$ or Fab fragment of the monoclonal antibody is administered.

9. A method of claim 5, wherein the radiolabel is Iodine-131, Indium-111 or Technetium-99m.

10. A method of claim 5, wherein the photoscanning device is a gamma-camera.

11. A method of diagnosing small carcinoma of the lung or a neuroblastoma, comprising the steps of:

a. contacting a tissue specimen from a patient suspected of being afflicted with small cell carcinoma of the lung or a neuroblastoma with an antibody which specifically reacts with the dihydropyridine-sensitive calcium channel; and b. determining whether the antibody binds to cells of the tissue specimen by immunohistochemical techniques, the binding of the antibody being an indication of the presence of small cell carcinoma of the lung or a neuroblastoma.

12. A method of diagnosing small cell carcinoma of the lung or a neuroblastoma, comprising the steps of:

a. contacting a tissue specimen from a patient suspected of being afflicted with small cell carcinoma of the lung or a neuroblastoma, with an antibody which specifically reacts with the 200 kDa polypeptide of the dihydropyridine-sensitive calcium channel; and b. determining whether the antibody binds to cells of the tissue specimen by immunohistochemical techniques, the binding of the antibody being an indication of the presence of small cell carcinoma of the lung or a neuroblastoma.

13. A method of claim 12, wherein the antibody is mab 1A produced by hybridoma cell line ATCC No. HB 10047.

14. A method of claim 12 wherein the immuno-histochemical technique is the immuno-fluorescent technique.

* * * * *